United States Defensive Publication [19] (H) [11] T101,601

Lau [43] Mar. 2, 1982

[54] CYAN DYE-FORMING COUPLERS

[76] Inventor: Philip T. S. Lau, c/o Kodak Park Works, Rochester, N.Y. 14650

[21] Appl. No.: 280,594

[22] Filed: Jul. 6, 1981

Related U.S. Application Data

[60] Division of Ser. No. 168,831, Jul. 10, 1980, which is a continuation-in-part of Ser. No. 85,140, Oct. 15, 1979, abandoned.

[51] Int. Cl.[3] ..... C07C 39/04

[52] U.S. Cl. ..... 568/716; 430/17; 430/384; 430/385; 430/552; 430/553

[57] ABSTRACT

Novel phenolic cyan dye-forming couplers contain in the 2-position a p-cyanophenylureido group. These couplers are useful in photographic emulsions, elements and processes.

6 Claims, No Sheets Drawing,

28 Pages Specification

The file of this unexamined application may be inspected and copies thereof may be purchased (849 O.G. 1221, Apr. 9, 1968).